(12) United States Patent
Dimmer et al.

(10) Patent No.: US 9,090,929 B2
(45) Date of Patent: Jul. 28, 2015

(54) MEDIUM FOR DETECTING AND DIFFERENTIATING VANCOMYCIN-RESISTANT ENTEROCOCCI

(75) Inventors: Stephen Dimmer, Chandlers Ford (GB); Dagmara Klein, Basingstoke (PL)

(73) Assignee: Oxoid Limited, Hampshire (GB)

( * ) Notice: Subject to any disclaimer, the term of this patent is extended or adjusted under 35 U.S.C. 154(b) by 1083 days.

(21) Appl. No.: 12/613,834

(22) Filed: Nov. 6, 2009

(65) Prior Publication Data

US 2010/0120086 A1    May 13, 2010

(30) Foreign Application Priority Data

Nov. 7, 2008  (GB) .................................. 0820398.6
Dec. 15, 2008 (GB) .................................. 0822764.7

(51) Int. Cl.
*C12N 1/20* (2006.01)
*C12Q 1/20* (2006.01)
*C12Q 1/04* (2006.01)

(52) U.S. Cl.
CPC . *C12Q 1/045* (2013.01); *C12N 1/20* (2013.01)

(58) Field of Classification Search
CPC .................................. C12N 1/20; C12Q 1/045
See application file for complete search history.

(56) References Cited

U.S. PATENT DOCUMENTS

| | | | |
|---|---|---|---|
| 5,464,755 A * | 11/1995 | Bochner | 435/34 |
| 5,534,415 A | 7/1996 | Orenga | |
| 5,620,865 A | 4/1997 | Chen et al. | |
| 5,635,367 A | 6/1997 | Lund | |
| 5,846,761 A | 12/1998 | Rambach | |
| 5,962,251 A | 10/1999 | Rambach | |
| 6,165,743 A | 12/2000 | Rambach | |
| 6,355,449 B1 | 3/2002 | Chen et al. | |
| 6,548,268 B1 | 4/2003 | Rambach | |
| 6,905,841 B2 | 6/2005 | Desmonceaux et al. | |
| 7,192,734 B2 * | 3/2007 | Ohresser | 435/34 |
| 7,217,536 B2 | 5/2007 | Gilbert et al. | |
| 7,351,548 B2 | 4/2008 | Rambach | |
| 2002/0031796 A1 * | 3/2002 | Townsend et al. | 435/34 |
| 2002/0132285 A1 * | 9/2002 | Chen et al. | 435/34 |
| 2008/0145879 A1 | 6/2008 | Orenga et al. | |
| 2008/0145881 A1 * | 6/2008 | Kircher et al. | 435/18 |

FOREIGN PATENT DOCUMENTS

| | | |
|---|---|---|
| GB | 2407584 | 4/2005 |
| WO | WO 98/04674 | 2/1998 |
| WO | WO 2008/006816 | 1/2008 |
| WO | WO 2008/076452 A1 | 6/2008 |

OTHER PUBLICATIONS

Sarantinopoulos et al., Citrate metabolism by Enterococcus faecalis FAIR-E 229, Applied and Environmental Microbiology, 2001, p. 5482-5487.*

Huycke et al., Enterococus faecalis produces extracellular superoxide and hydrogen peroxide that damages colonic epithelial cell DNA, Carcinogenesis, vol. 23, p. 529-536, 2002.*

Lee et al., Characterization of Enterococcus faecalis Alkaline Phosphatase and Use in Identifying Streptococcus agalactiae, vol. 181, No. 18, Sep. 1999, pp. 5790-5799.

UK Combined Search and Examination Report, Apr. 14, 2009, 7 pages.

* cited by examiner

*Primary Examiner* — Taeyoon Kim
*Assistant Examiner* — Tiffany Gough
(74) *Attorney, Agent, or Firm* — Thompson Hine LLP (57) ABSTRACT

A medium for the growth of vancomycin-resistant *Enterococci* comprising:—
 (i) a nutrient medium with an energy source effective to support growth and reproduction of vancomycin-resistant *Enterococci;*
 (ii) an effective amount of one or more selective agents to inhibit the growth of microorganisms other than vancomycin-resistant *Enterococci;*
 (iii) a Krebs cycle intermediate.

19 Claims, 6 Drawing Sheets

FIG 1A

○ = blue

◍ = dark pink to violet

MEDIUM FOR DETECTING AND DIFFERENTIATING VANCOMYCIN-RESISTANT ENTEROCOCCI

This application claims priority to GB0820398.6 filed on Nov. 7, 2008 and GB0822764.7 filed on Dec. 15, 2008, each of which is expressly incorporated by reference herein.

The present invention relates to a medium for the growth and/or identification of microorganisms, and to a method of identification of microorganisms using the medium. More particularly, the present invention relates to a medium for detecting and differentiating different strains of bacteria. It is particularly applicable, but in no way limited, to media for detecting and differentiating different strains of vancomycin-resistant *Enterococci* and to methods for their differentiation and identification.

The detection and identification of microorganisms is very important in several fields, such as diagnosis of infectious disease, tracing sources of outbreaks of disease or contamination, and detecting and tracing the spread of antibiotic resistance etc.

Many methods of detecting and identifying microorganisms have been derived in recent years, employing sophisticated techniques, such as PCR and the like. While these methods may be rapid and sensitive, there is still a need for more traditional methods involving the culturing of organisms on media (especially solid media). These traditional methods have the great advantage that they result in isolation of organisms of interest in viable form, which can then be sub-cultured into other media and/or further analysed.

In humans and many other mammals, *Enterococci* are normally present in the oral cavity and gastrointestinal tract although typically in lower concentrations than *E. coli. Enterococci* often grow as pairs or chains and can thrive in culture in the presence of bile salts or sodium azide at concentrations that are inhibitory to coliform bacteria and many Gram-negative bacteria. *Enterococci* have frequently shown resistance to certain antibiotics including penicillin and aminoglycosides, making vancomycin, a glycopeptide antibiotic, the antibiotic of choice for treating patients with enterococcal infections.

In the past two decades, glycopeptide-acquired resistance in *Enterococci* populations has increased. In particular, vancomycin-resistant *Enterococci* (VRE) have become associated with high mortality rates and are a common form of infection in hospital intensive care units. In particular, acquired resistance, encoded by vanA or vanB genes, is considered a serious health threat especially since transfer of these genes may occur via plasmids and transposons to other pathogenic bacteria including *Staphylococci*. Acquired resistance is associated with *E. faecalis* and *E. faecium* while *E. casseliflavus* and *E. gallinarum* generally express a non-transferable or intrinsic type of resistance encoded by vanC genes. Moreover, *E. faecalis* and *E. faecium*, whether sensitive or resistant to vancomycin, show differences in their sensitivity to other antibiotics. Therefore, detection of *Enterococci* and differentiation of species is important in determining antibiotic therapies to treat and control infections.

Several culture media have been developed for detecting VRE. One such medium is bile esculin agar with vancomycin (BEAv). *Enterococci* hydrolyze the glycoside, esculin, to form dextrose and esculitin. Esculitin reacts with ferric citrate or other ferrous ions in the medium to form a dark brown or black ring of iron phenolic compounds around each colony. Bile salts are added to inhibit growth of Gram-positive bacteria (other than group D streptococci) and sodium azide is included to inhibit growth of Gram-negative bacteria. BEAv permits detection of *Enterococci* but not differentiation of species because all *Enterococci* are capable of hydrolyzing esculin.

Therefore, media for growing and detecting *Enterococci* in general and even for detecting vancomycin-resistant *Enterococci* (VRE) in particular are known. However, VRE generally grow poorly on these media and the colonies produced are small and may take 48 hours or more to develop.

Furthermore most known media do not distinguish species. Instead most of the prior art discloses use of substrates that substantially all *Enterococci* species utilize. Distinction of species is important for several reasons. First, *E. gallinarum* and *E. casseliflavus* generally have a non-transmittable form of vancomycin resistance (encoded by the vanC gene) that is of little clinical importance while, in contrast, *E. faecium* and *E. faecalis* generally have a transferable form of resistance which is capable of transmission to other more aggressive pathogens, such as *Staphylococci*. Secondly, *E. faecium* and *E. faecalis* differ in their sensitivity to other antibiotics (when vancomycin is no longer an option due to resistance) and therefore, in order to effectively treat a patient, and stop the spread of VRE, it is important to distinguish between these two species to determine the appropriate antibiotic therapy.

U.S. Pat. No. 5,620,865 to Chen et al discloses a medium for growing and detecting *Enterococci* within 24 hours. The medium is based upon a formula comprising a nutrient indicator that releases a nutrient moiety in the presence of β-glucosidase enzyme which is universal to all *Enterococci* species and, therefore, does not allow for identification of species.

U.S. Pat. No. 6,355,449 to Chen et al discloses a so-called improved medium for detecting the presence of VRE comprising vancomycin, one or more selective agents for suppressing growth of unwanted fungi and bacteria, a first nutrient indicator which provides a first detectable signal when cleaved by a β-glucosidase and a second nutrient indicator which provides an intermediate molecule when cleaved by pyrrolidonyl arylamidase, wherein the intermediate molecule provides a second detectable signal upon reacting with a developing agent. Alternatively, the second nutrient indicator may provide a second detectable signal when cleaved by pyrrolidonyl arylamidase. Because β-glucosidase is common to all species of *Enterococci* and is also present in a number of other bacteria genera including *Listeria, Klebsiella*, and *Enterobacter*, a second enzyme common to *Enterococci* is targeted to increase the probability that identified microorganisms are *Enterococci*. However the use of two different enzymes as disclosed by Chen et al. does not distinguish between species of VRE.

A commercial product for culturing VRE is provided as CHROMagar™ VRE medium (CHROMagar Microbiology, Paris, France). The medium utilizes two chromogenic substrates and is capable of distinguishing *E. faecalis* and *E. faecium* from *E. gallinarum* and *E. casseliflavus* but not *E. faecalis* from *E. faecium.*

Another commercial product, chromID™ VRE (bioMerieux, France), is a solid nutrient medium comprising vancomycin (8 mg/L) and two chromogenic substrates, one hydrolyzed by α-glucosidase and the other by β-galactosidase, and is theoretically capable of distinguishing between *E. faecalis* and *E. faecium*. However, most colonies are small after 24 hours and difficult to observe visually if the original sample contained only a small number of *Enterococci*. Furthermore, growth of VRE arising from vanB genes is poor because of the high (8 mg/ml) vancomycin concentration. Since vanB causes a transmissible form of vancomycin resistance, it is important to be able to grow vanB VRE. Additionally, the colour of *E. faecalis* colonies grown in this medium is frequently inconsistent, increasing the risk of misidentification. *E. faecalis* is supposed to produce a blue-green colour but in practice the colour is inconsistent. Also, break-through growth by certain yeasts has been observed and this may cause false positive interpretations.

Molecular methods such as polymerase chain reaction (PCR) and cycling probe technology are available for the detection of vancomycin resistance genes. These methods offer a high degree of sensitivity and specificity as well as decreased turn around time compared to routine culture. However, they often only detect the van genes and do not provide a species level identification. In addition, many laboratories do not have the facilities, training or volume to justify performing such costly, complex procedures. Moreover, PCR may not be directly applicable for use with a typical patient specimen containing a mixed population of microorganisms, particularly if the target microorganism is present in small numbers. Thus, pre-culture of specimens may be needed to enrich for and/or isolate particular microorganisms before undertaking PCR assays.

Identification (ID) to the species level can be accomplished using a commercially available automated or manual ID system, although it has been noted that some of the commercial systems may not always accurately identify *E. faecium*. All of these systems require a pure isolate and can take up to 24 hours to obtain a definitive identification.

Current methods for detecting and identifying VRE at the species level require either a pure isolate and or multiple tests. Thus, a method for speciating *Enterococci* rather than providing a genus level identification from the original patient specimen is desired.

There is therefore a long-felt need in the industry to provide a medium capable of distinguishing between *Enterococci* species, and that can provide consistent, easy to interpret results within 24 hours.

Traditionally, most microbiological culture media formulations, because of the component ingredients, have been substantially transparent. Recently, use of media containing chromogenic or fluorogenic substrates susceptible to hydrolysis by particular enzymes characteristic of certain microorganisms and, therefore, useful for identifying microorganisms, including bacteria, yeasts and fungi, has become increasingly popular. Examples of such media are described in U.S. Pat. No. 5,534,415, U.S. Pat. No. 5,635,367, U.S. Pat. No. 5,846,761, U.S. Pat. No. 5,962,251, U.S. Pat. No. 6,165,743, U.S. Pat. No. 6,905,841, U.S. Pat. No. 7,217,536 and U.S. Pat. No. 7,351,548, the text of all of which are hereby incorporated herein in entirety and intended to be an integral part of this disclosure.

Use of chromogenic (or fluorogenic) media necessitates the need for greater contrast between colony colours and background colour of the medium. Many manufacturers of chromogenic (or fluorogenic) culture media have begun to add opacifying agents, such as kaolin or titanium dioxide, to increase the opacity of media and the contrast with the coloured colonies, thereby facilitating detection of the colonies. Improved detection and identification of colonies lowers the risk of misdiagnosis.

However, while addition of opacifying agents improves the usefulness of media containing chromogenic (or fluorogenic) substrates, use of an opaque medium obscures information written, printed or otherwise applied to the bottom of the culture dish. Often such information is necessary for the proper identification of the culture and necessitates additional handling of the culture dish to move it into a position so that the information can be read or otherwise detected because the opacity of the medium prevents accurate reading or other optical detection through the medium. Extra manipulation of culture dishes requires time and risk of dropping or otherwise adversely affecting the culture. Yet it is important to access the information because improved detection of information lowers the risk of misidentification and other confusion.

The terms "chromogenic substrate" and "fluorogenic substrate" are well known to those skilled in the art and refer to chemical compounds which are cleaved by enzymes produced by some bacteria and which, as a result of that cleavage, give colouration or fluorescence to certain bacteria colonies.

According to a first aspect of the invention there is provided a medium for the growth of vancomycin-resistant *Enterococci* comprising:—
 (i) a nutrient medium with an energy source effective to support growth and reproduction of vancomycin-resistant *Enterococci;*
 (ii) an effective amount of one or more selective agents to inhibit the growth of microorganisms other than vancomycin-resistant *Enterococci;*
 (iii) a Krebs cycle intermediate.

Incorporation of a Krebs cycle intermediate encourages growth of vancomycin-resistant *Enterococci*, such that meaningful test results can be obtained in 24 hours or less.

Preferably the Krebs cycle intermediate is selected from one or more of the group comprising:—
 α-ketoglutaric acid and salts and derivatives thereof;
 D-isocitric acid and salts and derivatives thereof;
 citric acid and salts and derivatives thereof;
 oxaloacetic acid and salts and derivatives thereof;
 malic acid and salts and derivatives thereof;
 fumaric acid and salts and derivatives thereof;
 succinic acid and salts and derivatives thereof;
 cis-aconitic acid and salts and derivatives thereof; and
 succinyl-CoA In this context the term derivative includes any chemical compound in which the key structural elements of the parent compound is present and which is converted to the desired Krebs cycle intermediate in the nutrient medium or in the presence of the microorganism. Such derivatives include, for example, lower alkyl esters, which are de-esterified by esterases present in the medium or in the microorganism.

Preferably the Krebs cycle intermediate includes α-ketoglutaric acid and/or salts, derivatives, and precursors thereof. Precursors to α-ketoglutarate include pyruvic acid and salts and derivatives thereof; acetyl CoA; cis-aconitic acid and salts and derivatives thereof; and D-isocitric acid and salts and derivatives thereof. α-ketoglutarate has been found to be a particularly effective intermediate for encouraging growth of vancomycin-resistant *Enterococci*.

Inclusion of one or more Krebs cycle intermediates such as α-ketoglutaric acid and salts or derivatives thereof improves growth response by acting as a growth promoter. This results in larger colonies at 24 hours improving identification of the presence of bacterial colonies. Use of Krebs cycle intermediates as growth promoters has not previously been disclosed for *Enterococci* microorganisms. By improving the detection of the *Enterococci* any necessary clinical intervention can be made more quickly.

Preferably the medium further comprises an opacifying agent and preferably the opacifying agent is kaolin or titanium dioxide and the opacifying agent is present in a concentration range of between 0.1 g-5 g/L of medium.

Preferably the selective agent is selected from one or more of the group comprising:—
 a glycopeptides antibiotic including teicoplanin or vancomycin;

an antifungal compound;
aztreonam;
erythromycin;
polymyxin B and salts thereof;
cefoxitin;
amphotericin B.

Use of a glycopeptide antibiotic prevents the growth of microorganisms other than those resistant to such an antibiotic, and ensures that only resistant microorganisms give rise to colonies. In this way, the presence of a colony indicates that vancomycin-resistant microorganisms are present. The selective agents may be chosen so as to inhibit the growth of Enterococci with intrinsic, non-transferable resistance (vanC) to vancomycin such as E. gallinarum, E. casseliflavus and E. arium as well as yeasts, lactic acid bacteria and non-VRE Gram-positive and Gram-negative bacteria.

Vancomycin may be used at a level that allows growth of vanB resistant organisms. This allows the presence of these clinically important organisms to be detected. Preferably vancomycin is used at a concentration of less than 8 mg/L, more preferably 3 to 7 mg/L, most preferably around 5 to 6 mg/L.

The medium may also comprise further selective agents such as antifungal compounds to prevent overgrowth of the medium with other microorganisms. Further selective agents may be selected from other antibiotics including for example β-lactam antibiotics and cephalosporins. Examples of further suitable antibiotic and antifungal compounds which may be useful as selective agents in the present invention include aztreonam, erythromycin, polymyxin B sulphate, colistin, cefoxitin and amphotericin B.

Chromogenic or fluoregenic substrates incorporating a phosphate group and/or a galactopyranosyl group may advantageously be added to this medium as described below in order that the medium may be used to detect and differentiate between different species of vancomycin-resistant Enterococci. This aspect of the invention is described in more detail below.

According to a second aspect of the present invention there is provided a medium for detecting vancomycin-resistant Enterococci comprising:—
(a) a nutrient medium with an energy source effective to support growth and reproduction of vancomycin-resistant Enterococci;
(b) an effective amount of one or more selective agents to inhibit the growth of microorganisms other than vancomycin-resistant Enterococci;
(c) a first chromogenic substrate incorporating a phosphate group and which is a substrate for a phosphatase enzyme produced by a first vancomycin-resistant Enterococcus species, said first chromogenic substrate producing a first detectable signal when in the presence of said first vancomycin-resistant Enterococcus species; and
(d) a second chromogenic substrate incorporating a galactopyranosyl moiety which is a substrate for a galactopyranoside enzyme produced by a second vancomycin-resistant Enterococcus species, said second chromogenic substrate producing a second detectable signal when in the presence of said second vancomycin-resistant Enterococci species.

By utilising a chromogenic substrate comprising a phosphate group, the detectable signal is produced only in the presence of a microorganism which produces a specific phosphatase enzyme that can metabolise that phosphate compound. In the presence of a phosphatase enzyme, the chromogenic substrate comprising a phosphate group is metabolized producing the detectable signal. Enterococci species differ in their ability to metabolize phosphate compounds and as the detectable signal will only be produced in the presence of a bacterial species capable of metabolizing phosphate, the medium can be used to distinguish between species of Enterococci bacteria.

Phosphatase enzymes remove phosphate groups from a substrate by hydrolysing a phosphoric acid monoester into a phosphate ion and a molecule with a free hydroxyl group.

Alkaline phosphatase is a hydrolase enzyme responsible for removing phosphate groups from many types of molecules.

The chromogenic substrates are provided in an amount sufficient to allow a detectable characteristic signal to be produced in the medium by the growth of the Enterococcus species specific for the chromogenic substrate.

The first chromogenic substrate is preferably used at a concentration range of 0.05 to 0.4 g/Lm more preferably 0.1 to 0.35 g/L. Most preferably the first chromogenic substrate is used at a concentration of 0.3 g/L.

A preferred second chromogenic substrate is a substrate comprising a galactopyranoside group. These substrates may be metabolized by galactopyranosidase enzymes to produce a coloured compound. An example of a suitable chromogenic substrate is 6-chloro-3-indolyl-α-galactopyranoside. Preferably this is used at a concentration range of 0.05 to 0.4 g/L. More preferably, this is used at a concentration of 0.1 to 0.3 g/L, most preferably 0.15 g/L.

Preferably the detectable signals are visual signals observable by the naked eye.

Most preferably, the chromogenic substrates react in the presence of an Enterococcus species to produce a detectable signal comprising a coloured compound such that the bacterial colonies appear coloured. The presence of an Enterococcus species can therefore be confirmed by a simple visual assessment of the medium.

By utilising two chromogenic substrates, each of which produces a particular colour when metabolised by a particular bacterial species, the medium allows the presence of a particular bacterial species to be detected and also two different species to be differentiated.

The invention is particularly useful for the detection and differential identification of the clinically important Enterococci species E. faecalis and E. faecium. Use of a phosphate-based chromogenic substrate results in a reliable, consistent colour to the colony, minimising the likelihood of misidentification due to variable colour production. E. faecalis metabolises the phosphate-based chromogenic substrate resulting in a coloured bacterial colony. E. faecium metabolises the second chromogenic substrate resulting in a bacterial colony of a different colour. When, for example, the first chromogenic substrate is 5-bromo-3-indolyl phosphate disodium salt, and the second is 6-chloro-3-indolyl-α-galactopyranoside, E. faecium produces pinkish-purple (magenta) colonies and E. faecalis is indicated by the presence of blue colonies.

Thus, the medium of the present invention allows for E. faecium and E. faecalis to be detected and differentiated quickly and reliably.

Preferably the medium further comprises a Krebs cycle intermediate, most preferably α-ketoglutarate. Inclusion of a Krebs cycle intermediate such as α-ketoglutaric acid improves growth response by acting as a growth promoter. This results in larger colonies at 24 hours improving identification of the presence of bacterial colonies. Use of Krebs cycle intermediates as growth promoters has not previously been disclosed for Enterococci microorganisms. By improving the detection of the Enterococci any necessary clinical intervention can be made more quickly.

The Krebs cycle (or citric acid cycle or tricarboxylic acid (TCA) cycle) is a series of enzyme-catalysed chemical reactions of central importance to cells that respire using oxygen. Pyruvate (from glycolysis) is converted to acetyl CoA which feeds into the cycle. This reacts with oxaloacetate to form citrate. This is converted to cis-aconitate, then isocitrate, followed by conversion to alpha-ketoglutarate and then sequentially succinyl CoA, succinate, fumarate and malate before regenerating oxaloacetate.

Preferably the Krebs cycle intermediate is selected from one or more of the group comprising:—
  α-ketoglutaric acid and salts and derivatives thereof;
  isocitric acid and salts and derivatives thereof;
  citric acid and salts and derivatives thereof;
  oxaloacetic acid and salts and derivatives thereof;
  malic acid and salts and derivatives thereof;
  fumaric acid and salts and derivatives thereof;
  succinic acid and salts and derivatives thereof; and
  aconitic acid and salts and derivatives thereof.

Optionally, visualization is facilitated by using a culture medium or a culture dish that provides enhanced contrast when chromogenic (or fluorogenic) substrates are used, yet permits the visualization or other optical detection through the medium of information applied to the bottom of the culture dish. For example, the medium may comprise an opacifying agent. Preferably the opacifying agent is kaolin or titanium dioxide at a concentration of 0.1-0.5 g/L of medium Alternatively, the medium may be contained within a culture dish which has a bottom surface that has been chemically or physically altered to be semi-opaque without obscuring visualisation of the bottom of the dish.

Preferably the selective agent is selected from one or more of the group comprising:—
  a glycopeptide antibiotic including teicoplanin or vancomycin;
  an antifungal compound;
  aztreonam;
  erythromycin;
  polymyxin B and salts thereof;
  cefoxitin;
  amphotericin B.

Use of a glycopeptide antibiotic prevents the growth of microorganisms other than those resistant to such an antibiotic, and ensures that only resistant microorganisms give rise to colonies. In this way, the presence of a colony indicates that vancomycin-resistant microorganisms are present. The selective agents may be chosen so as to inhibit the growth of Enterococci with intrinsic, non-transferable resistance (vanC) to vancomycin such as *E. gallinarum, E. casseliflavus* and *E. arium* as well as yeasts, lactic acid bacteria and non-VRE Gram-positive and Gram-negative bacteria.

Vancomycin may be used at a level that allows growth of vanB resistant organisms. This allows the presence of these clinically important organisms to be detected. Preferably vancomycin is used at a concentration of less than 8 mg/L, more preferably 3 to 7 mg/L, most preferably around 5 mg/L.

The medium may also comprise further selective agents such as antifungal compounds to prevent overgrowth of the medium with other microorganisms. Further selective agents may be selected from other antibiotics including for example β-lactam antibiotics and cephalosporins. Examples of further suitable antibiotic and antifungal compounds which may be useful as selective agents in the present invention include aztreonam, erythromycin, polymyxin B sulphate, colistin, cefoxitin and amphotericin B.

Preferably the first *Enterococci* species is *E. faecalis*. Preferably the second *Enterococci* species is *E. faecium*. These species of *Enterococcus* have the ability to acquire resistance to vancomycin and as such have become associated with high mortality rates. These species are therefore of particular clinical importance.

Preferably the first chromogenic substrate is selected from the list comprising:—
  5-bromo-3-indolyl-phosphate disodium salt or p-toluidine salt (blue);
  5-bromo-4-chloro-3-indolyl-phosphate disodium salt or p-toluidine salt (green blue);
  5-bromo-6-chloro-3-indolyl-phosphate disodium salt or p-toluidine salt (magenta);
  6-chloro-3-indolyl-phosphate disodium salt or p-toluidine salt (pink);
  3-indolyl-phosphate disodium salt or p-toluidine salt (blue); and
  Fluorogens 6-fluoro-3-indolyl-phosphate disodium salt or p-toluidine salt; and
  4-methylumbelliferyl-phosphate disodium salt or p-toluidine salt.

It will be appreciated that other suitable salts of these phosphate chromogenic substrates may also be used.

In a particularly preferred embodiment the first chromogenic substrate is 5-bromo-3-indolyl phosphate disodium salt.

Preferably the second chromogenic substrate is selected from the list comprising:—
  5-bromo-3-indolyl-α-galactopyranoside (blue);
  5-bromo-4-chloro-3-indolyl-α-galactopyranoside (green blue);
  5-bromo-6-chloro-3-indolyl-α-galactopyranoside (magenta);
  6-chloro-3-indolyl-α-galactopyranoside (pink);
  3-indolyl-α-galactopyranoside (blue); and
  Fluorogens 6-fluoro-3-indolyl-α-galactopyranoside; and
  4-methylumbelliferyl-α-galactopyranoside.

In a particularly preferred embodiment the second chromogenic substrate is 6-chloro-3-indolyl-α-galactopyranoside.

The *Enterococci* may be detected in a liquid or gel medium. The medium may also be semi-solid or solid. Gel based media may be prepared by adding agar to the medium as is well known to those skilled in the art. Before setting, the molten gel medium is poured into culture plates or dishes. Once set, the plates are inoculated with the sample of interest. This may be a clinical sample including without limitation a stool sample, rectal swab, peri-rectal swab, urine or serum, an environmental sample such as a food sample or surface contact swabs from areas such as doorknobs, walls and counter tops.

According to the present invention there is also provided a method of screening for and differentiating between *E. faecalis* and *E. faecium* comprising inoculating a medium according to the invention with a biological specimen, incubating to obtain growth of *Enterococci* and examining the medium for the first and second detectable signals.

Typically the inoculated medium is incubated at 33-39° C., preferably 37° C., for approximately 22 to 26 hours, most preferably 24 hours. If the results are negative after this first incubation, the medium is incubated for an additional 24-hour period. The presence of vancomycin-resistant *Enterococci* is determined by observation of the detectable signals.

For example, the presence of *E. faecalis* is indicated by the presence of blue colonies whilst vancomycin-resistant *E. faecium* produces pinkish-purple (magenta) colonies when the first chromogenic substrate is 5-bromo-3-indolyl phosphate disodium salt and the second is 6-chloro-3-indolyl-α-galactopyranoside.

It will be understood that where a vancomycin-resistant *Enterococci* species is present which contains both a phosphatase enzyme and a galactopyranosidase enzyme, then both chromogens will be produced and the species will be coloured in a colour which is a mixture of the two different chromophore colours. Thus different *Enterococci* will cause certain different shades of colour to be produced. This grading of the colour response provides both a means of identification and a means of differentiation between different vancomycin-resistant *Enterococci*.

It will also be appreciated that it is not essential, although it is desirable, to include both a first and a second chromogenic substrate. Various possible combinations are set out in Table I below.

(i) a chromogenic substrate comprising a phosphate group (ii) an opacifying agent (iii) a Krebs cycle intermediate compound.

Use of a phosphate-based substrate produces a more consistent colour reaction. For example, in the presence of *E. faecalis* and 5-bromo-3-indolyl phosphate, a consistent blue colour is produced. The use of opacifying agents enhances contrast between the chromogens and the background. This improves visual detection allowing results to be obtained earlier. The use of a Krebs cycle intermediate (such as α-ketoglutaric acid) as a growth factor results in colonies that are larger and easier to view at 24 h.

TABLE I

Possible combinations of phosphate, galactopyranoside and selective agent(s)

| | | |
|---|---|---|
| Phosphate Vancomycin No alpha-galactopyranoside | Two VRE species (*faecium, faecalis*) detected, no species differentiation | Colony colour depends on the phosphate chromophore used (e.g. blue, pink, magenta, turquoise) |
| Alpha-galactopyranoside Vancomycin No phosphate | Two VRE species (*faecium, faecalis*) detected, potential species differentiation or detection of *E. faecium* only (if antibiotics adjusted) | Colony colour: *E. faecalis* - colourless, *E. faecium* - depending on the alpha-gal used (e.g. blue, pink, magenta, turquoise) |
| Vancomycin No phosphate No alpha-galactopyranoside | Two VRE species (*faecium, faecalis*) detected, no species differentiation | Colourless colonies |
| Phosphate Alpha-galactopyranoside No vancomycin | Medium for resistant and non-resistant enterococci detection (e.g. in water?); could distinguish between *faecium* and *faecalis* but it is difficult to predict what other enterococci could grow through | Colony colours depending on chromogens used |
| Phosphate Alpha-galactopyranoside Vancomycin No erythromycin | Medium for VRE and lactic acid bacteria (LAB) (highly improbable requirement) | LAB colonies can uptake both chromogens (predominantly phosphate) |
| Phosphate Alpha-galactopyranoside Vancomycin No cefoxitin | Medium for VRE (including VanC like *E. gallinarum, casseliflavus* depending on actual MIC - vancomycin). VanC could be distinguished based on the shade of purple. | *E. gallinarum, casseliflavus* can uptake both chromogens |
| Phosphate Alpha-galactopyranoside Vancomycin No KGA | Two VRE species (*faecium, faecalis*) detected, significantly smaller colonies, slower chromogen uptake (especially pink), more chromogen needed in the formulation, inhibited growth, extended time of incubation needed. | Colony colours depending on chromogens used (colours may need up to 48 h to develop) |

According to a further aspect of the invention, there is also provided a medium for detecting vancomycin-resistant *Enterococci* comprising:—

(a) an effective amount of one or more selective agents to inhibit the growth of microorganisms other than vancomycin-resistant *Enterococci*; and (b) two or more components selected from the group consisting of:—

Two or more of these components are selected for use in the medium. This allows the characteristics of the medium to be tailored to particular requirements.

According to a yet further aspect of the invention there is provided a prepared culture medium in a culture dish, wherein the medium is semi-opaque. In yet further embodiments, the culture dish may be semi-opaque or the bottom wall of the dish supporting the medium may be semi-opaque or at least one or more selected areas of the bottom wall may be semi-opaque. Alternatively, the invention is a combination of semi-opaque culture medium contained within a semi-opaque dish. The medium or culture dish may also be used to culture one or more specimens from a patient.

Therefore, according to one further aspect of the invention, there is provided a culture medium, contained within a culture dish, comprising a nutrient medium for supporting the growth of one or more microorganism and containing:
 at least one of a chromogenic substrate or a fluorogenic substrate, and an opacifying agent in an amount sufficient to increase the opacity of the medium without obscuring visualization of the bottom of the dish.

Also provided is a culture medium, contained within a culture dish, comprising:—
 a nutrient medium for supporting the growth of one or more microorganisms, and
 at least one of a chromogenic substrate or fluorogenic substrate,
 wherein said dish has a bottom surface that has been chemically or physically altered to be semi-opaque without obscuring visualization of the bottom of the dish.

Semi-opaque dishes may be prepared in a number of ways including, without limitation, addition of an opacifying agent, such as titanium dioxide or other substantially white pigment, to the plastic resin prior to moulding the dish in an amount sufficient to reach the desired level of semi-opacity. Addition of chemicals to polymer resins, sometimes referred to as "doping", is common practice in the plastics industry and opacifying agents may be added according to methods known in the art.

Alternatively, the inner and/or outer surfaces of the culture dish may be mechanically or chemically etched, scored, ground, roughened or otherwise altered as is known in the art to render the bottom of the dish semi-opaque or to produce at least one semi-opaque region on the bottom of the dish. By "on the bottom of the dish" is meant the inner surface or outer surface of the bottom wall or a combination of both.

Semi-opaque medium can be prepared by adding an opacifying agent such as titanium dioxide or kaolin to the medium before it is allowed to solidify, in an amount sufficient to increase the opacity of the medium while still permitting the visualization of information contained on the bottom of a culture dish containing the semi-opaque medium. For example, titanium dioxide or kaolin or combinations thereof, may be added to most culture media formulations without adverse effect. These may be added at a concentration of 0.1-20 g/L, more preferably 0.1-5 g/L, most preferably 0.5 g-2 g/L. In particular, a range of 0.5 g-2 g/L titanium dioxide or kaolin is useful in improving visual contrast with many chromogenic or fluorogenic substrates.

A combination of a semi-opaque dish and semi-opaque medium may also be used. A dish having at least a portion of the bottom surface, whether inner or outer surface, treated mechanically or chemically to increase opacity, can be used to contain a medium containing a reduced amount of opacifying agent. For example, medium containing 0.1-1 g/L titanium dioxide or 0.1 g-1 g/L kaolin is useful when contained in a semi-opaque dish or dish with at least one semi-opaque area.

An optimal level of semi-opacity is dependent upon the chromogen or fluorogen used and the target microorganism(s) selected. As is known in the art, colonies may appear anywhere from pale to dark intensity with colours including various shades of pink, blue, beige, yellow, green, red, magenta, violet, purple, and so forth.

Figure 6A:
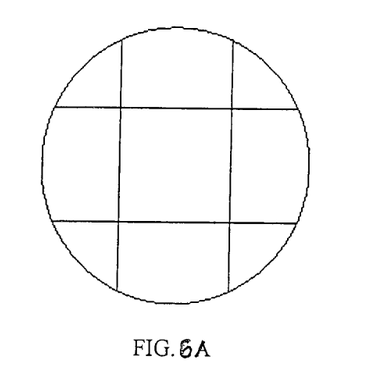
FIG. 6 depicts examples of the many variations possible for dividing the culture area.
Figure 6B:
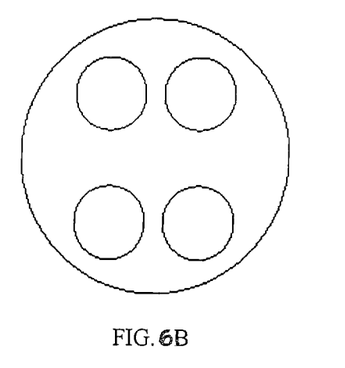
Figure 6C:
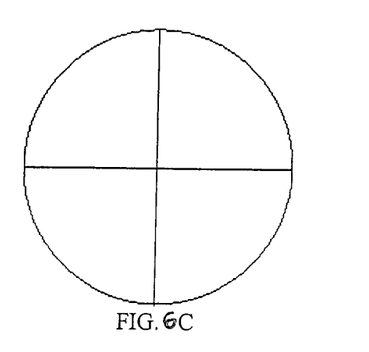

Use of a semi-opaque medium and/or a semi-opaque dish permits division of the culture area within the dish into multiple culture sites which, in turn, permits the testing of multiple samples from a patient within the same culture dish. By way of example, FIG. 6A-6C shows a few examples of the many variations possible for dividing the culture area so that multiple samples may be accommodated. Lines may be drawn, printed, etched, engraved, embossed or applied in any other method suitable for use with culture dishes.

The invention will now be illustrated by means of examples.

FIG. 2 depicts $E.\ faecium$ growing on agar plates.

FIG. 3 depicts a vanB strain growing on agar plates comprising ChromID VRE medium (FIG. 3A) and a medium according to the present invention (FIG. 3B);

FIG. 4 depicts $E.\ faecalis$ growing on agar plates comprising ChromID VRE (FIG. 4A) and a medium of the present invention (FIG. 4B);

FIG. 5 depicts $E.\ gallinarum$ growing on agar plates comprising ChromID VRE (bioMérieux) (FIG. 5A) and a medium of the present invention (FIG. 5B);

As used herein, the term "medium" (plural "media") refers to a solid, semi-solid, powder or liquid mixture, which contains all or substantially all of the components necessary to allow a microbe to grow and reproduce. The medium may be sterile or non-sterile as generally accepted practice requires.

As used herein, the term "biological specimen" refers to any sample taken from or coming from a substance that might be expected to contain bacteria and/or other microorganisms, and includes, but is not limited to, samples from the environment (eg soil or water), or samples from humans (eg clinical samples such as stool, rectal swabs, urine, blood, wounds).

As used herein, the term "microorganism" refers to microscopic organisms and include, but is not limited to, bacterial, fungi, yeasts, molds and viruses.

As used herein, the term "chromogenic substrate" or "chromogen" refers to a substrate conjugated to a chromophore. When cleaved from the substrate, the chromophore produces a visible colour. Similarly a fluorogenic substrate or fluorogen refers to a substrate coupled to a fluorophore. A fluorophore provides a fluorescent signal.

Chromogenic substrates react with an enzyme to produce a coloured compound. Chromogenic substrates may be made synthetically and may be designed to have a similar selectivity to the natural substrate for the enzyme. A coloured compound is produced when cleavage of the chromogenic substrate by the enzyme occurs. Similarly, fluorogenic substrates react to produce a fluorescent compound.

Figure 1A:
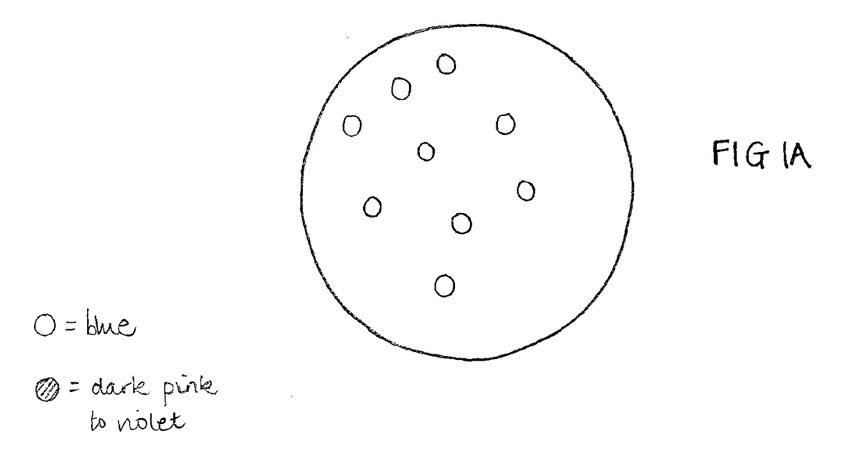
FIG. 1A depicts an agar plate visualizing blue colonies of $E.\ faecalis$.
Figure 1B:
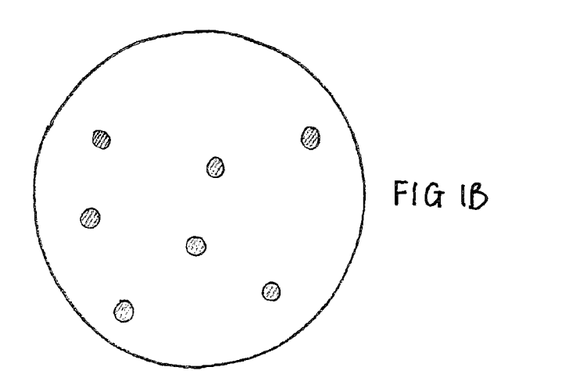
FIG. 1B depicts an agar plate visualizing dark pink to violet colonies of $E.\ faecium$.

FIG. 1 shows colonies of $E.\ faecalis$ (FIG. 1A, blue) and colonies of $E.\ faecium$ (FIG. 1B, dark pink to violet) growing on agar plates comprising the medium of the present invention.

The chromogenic substrates are 5-bromo-3-indolyl phosphate and 6-chloro-3-indolyl-α-galactopyranoside.

The colonies are well formed after 24 h incubation and the medium gives rise to consistent, readily identifiable coloured colonies allowing $E.\ faecalis$ and $E.\ faecium$ to be identified when present.

Figure 2A:
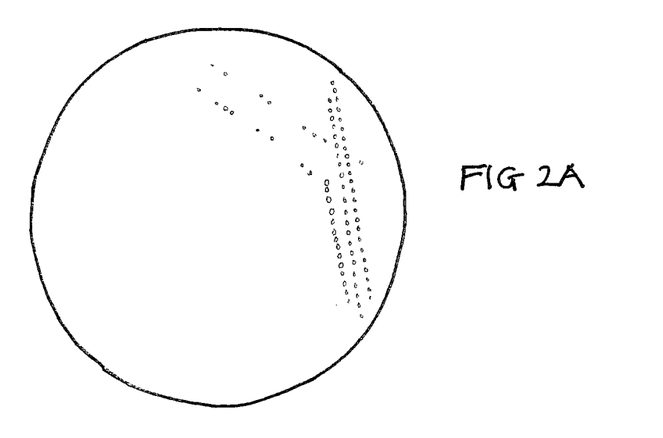
In FIG. 2A, the medium is ChromID VRE (bioMérieux, France).
Figure 2B:
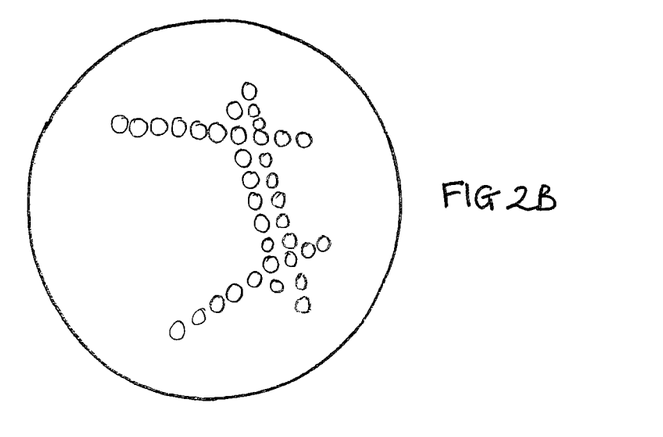
In FIG. 2B, the medium is a medium according to the present invention.

FIG. 2 depicts $E.\ faecium$ growing on ChromID VRE medium (FIG. 2A) and the medium of the present invention (FIG. 2B). The *E. faecium* colonies growing on the medium of the present invention are considerably bigger at 24 h. This illustrates one advantage of the present invention—that is that colonies are larger and therefore easier to identify after just 24 hours incubation.

Figure 3A:
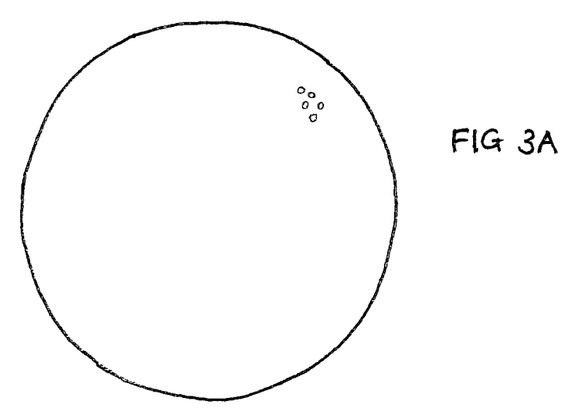
Figure 3B:
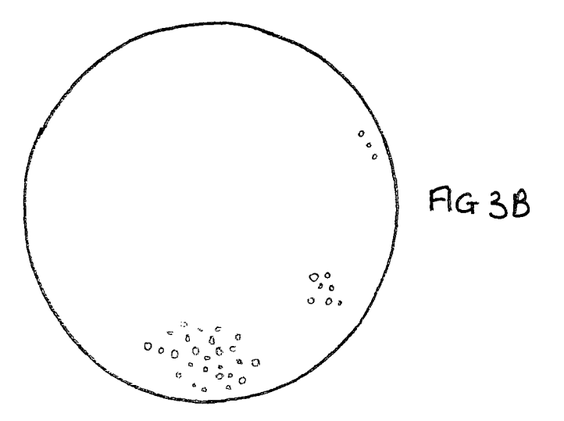

FIG. 3 depicts a vanB strain of *E. faecium* growing on ChromID VRE medium (FIG. 3A) and on a medium according to the present invention (FIG. 3B). Such vanB strains are considerably more inhibited on ChromID VRE medium than on the medium of the present invention. This illustrates a further advantage of the present invention, that is that vanB resistant organisms are detected using the medium of the present invention.

Figure 4A:
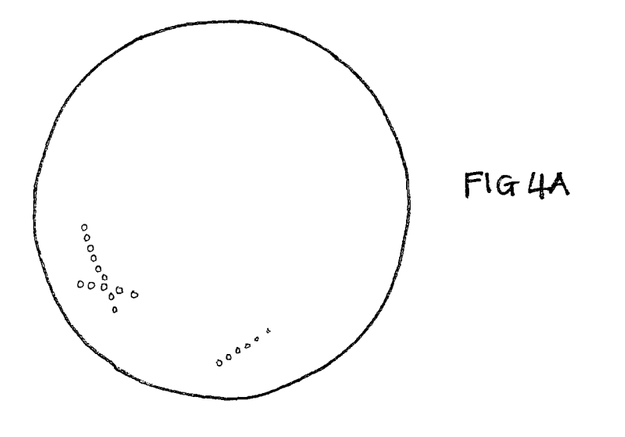
Figure 4B:
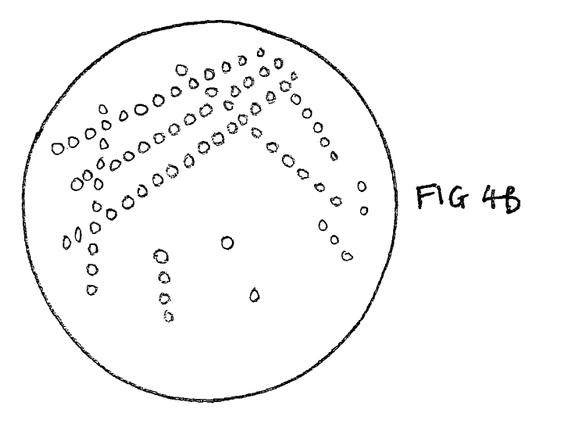

The medium of the present invention also results in larger *E. faecalis* colonies at 24 h when compared to existing media, as is illustrated by FIGS. 4A and 4B. FIG. 4A shows *E. faecalis* growing on ChromID VRE and FIG. 4B larger colonies on a medium of the present invention.

Figure 5A:
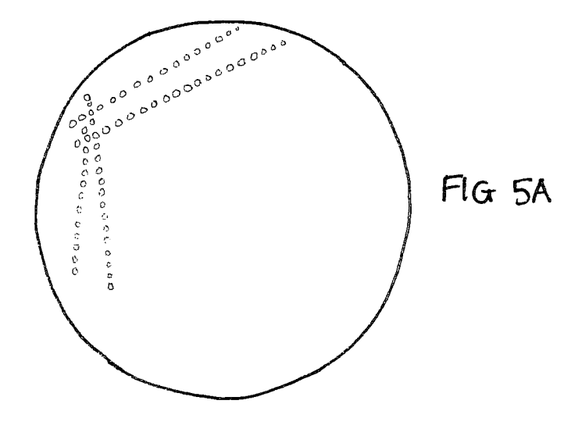
Figure 5B:
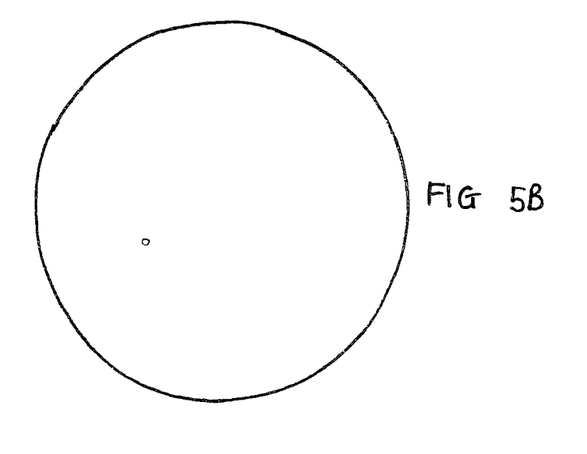

*E. casseliflavus* and *E. arium* are completely inhibited on the medium according to the present invention. *E. gallinarum* is not completely inhibited on ChromID VRE, (see FIG. 5A) but only single colonies may be observed after 48 h on the medium of the present invention (FIG. 5B).

Addition of an opacifying agent to the medium and/or use of a semi-opaque dish permits division of the culture area within the dish into multiple culture sites which, in turn, permits the testing of multiple samples from a patient within the same culture dish. A few examples of the many variations possible for dividing the culture area so that multiple samples may be accommodated are given in FIGS. 6A-6C. Lines may be drawn, printed, etched, engraved, embossed or applied in any other method suitable for use with culture dishes.

EXAMPLE 1

VRE Medium

VRE Base:

| Component | g/L | Potential range g/L | Substitutes |
|---|---|---|---|
| Dextrin | 0.86 | 0-5 | maltodextrin |
| sodium pyruvate | 0.09 | 0-10 | |
| NaOH | 0.083 | 0.01-0.5 | KOH |
| Microfine salt | 5.43 | 5-25 | NaCl |
| Streptococci Mix* | 4 | | |
| mycoprotein peptone | 0.4 | 0-5 | other peptones |
| Magnesium sulfate | 0.1 | 0.1-2 | |
| L-threonine | 0.2 | 0-5 | other amino acids |
| casein, peptic digest | 8.17 | 5-30 | |
| yogurt tryptone | 8.42 | 1-30 | tryptone |
| yeast extract, powder | 8.17 | 0-10 | |
| Agar | 12.50 | 10-16 | |
| Ketoglutaric acid | 1 | 0-10 | |
| Kaolin | 10 | 0.5-20 | titanium IV oxide |

*STREPTOCOCCI MIX (for approximately 100 Kg of stock mix):
Yeast extract powder: 64 Kg
Sodium pyruvate: 32 Kg
Uracil: 0.64 Kg
Adenine sulfate: 0.64 Kg
Pyridoxine HCl: 0.64 Kg
Folic acid: 0.064 Kg Antibiotics/Antifungal Mix:

| Component | mg/L | Potential range mg/L | Substitutes |
|---|---|---|---|
| vancomycin | 6 | 5-6 | teicoplanin |
| aztreonam | 18 | 4-30 | |
| erythromycin | 0.5 | 0.5-30 | |
| polymyxin B sulfate | 12.06 | | colistin |
| cefoxitin | 20 | 0.5-60 | cephalosporins |
| amphotericin B | 5 | 0.5-30 | other antifungals |

Chromogenic Substrates:
1. galactopyranoside-based chromogenic substrates in concentration range of 0.05 g/L to 0.4 g/L; example: 6-chloro-3-indolyl-α-galactopyranoside, 0.15 g/L
2. phosphate-based chromogenic substrate in concentration range of 0.05 g/L to 0.4 g/L; example: 5-bromo-3-indolyl phosphate, disodium salt, 0.3 g/L Exemplary Method of Making the Medium:
1. Add VRE base, 6-chloro-3-indolyl-α-galactopyranoside (0.15 g/L), and polysorbate 80 (0.2 ml) to 1 L of distilled water and mix gently (the mixture may be warmed during mixing but not boiled)
2. Sterilize via autoclaving (for example: 121° C. for 15 minutes)
3. Cool to about 50° C.
4. Supplement with antibiotic/antifungal mix and 5-bromo-3-indolyl phosphate, disodium salt (0.3 g/L), dissolved in small amount of appropriate solvent, as is known in the art, and filter sterilized before being added to cooled VRE medium
5. Pour into appropriate sterile culture dishes or containers
6. Allow to gel and dry, as is known in the art Exemplary Method of Using the Medium:
1. Inoculate plates with sample (may be clinical sample including without limitation, stool sample, rectal swab peri-rectal swab, urine or serum, or an environmental sample including without limitation, food samples, or swabs of surface contact areas such as doorknobs, walls, countertops, etc.). The sample may be 'streaked' onto the surface of an agar plate by dragging a suitable tool (such as an inoculation loop) across the surface of the agar plate.
2. Incubate at 33-39° C. for approximately 24 hours (22-26 hours); if results are negative, incubate an additional 24 hours.
3. Determine presence of vancomycin-resistant *E. faecalis* by presence of blue colonies and vancomycin-resistant *E. faecium* by presence of pinkish-purple (magenta) to purple colonies.

The invention claimed is:

1. A medium for the growth of vancomycin-resistant *Enterococci*, the medium comprising: (i) a nutrient medium with an energy source effective to support growth and reproduction of vancomycin-resistant *Enterococci*; (ii) an effective amount of at least one agent selective to inhibit the growth of microorganisms other than vancomycin-resistant *Enterococci*; and (iii) a Krebs cycle intermediate that includes a-ketoglutaric acid and salts thereof, the medium thus supporting the growth of vancomycin-resistant *Enterococci*.

2. The medium of claim 1 further comprising a Krebs cycle intermediate selected from at least one of the group comprising:
D-isocitric acid or salts thereof;
citric acid or salts thereof;
oxaloacetic acid or salts thereof;
malic acid or salts thereof;

fumaric acid or salts thereof;
succinic acid or salts and thereof;
cis-aconitic acid or salts thereof; and succinyl-CoA.

3. The medium of claim 1 further comprising an opacifying agent.

4. The medium of claim 3 wherein the opacifying agent is kaolin or titanium dioxide and the opacifying agent is present in a concentration range of between 0.1 g-5 g/L of medium.

5. The medium of claim 1, wherein the selective agent is selected from at least one of the group comprising: a glycopeptides antibiotic including teicoplanin; vancomycin; an antifungal compound; aztreonam; erythromycin; polymyxin B and salts thereof; cefoxitin; and amphotericin B.

6. The medium of claim 1 further comprising a first chromogenic substrate incorporating a phosphate group and which is a substrate for a phosphatase enzyme produced by a first vancomycin-resistant *Enterococcus* species, said first chromogenic substrate producing a first detectable signal when in the presence of said first vancomycin-resistant *Enterococcus* species.

7. The medium of claim 6 further comprising a second chromogenic substrate incorporating a galactopyranosyl moiety which is a substrate for a galactopyranoside enzyme produced by a second vancomycin-resistant *Enterococcus* specie, said second chromogenic substrate producing a second detectable signal when in the presence of said second vancomycin-resistant *Enterococci* species.

8. A medium for detecting vancomycin-resistant *Enterococci*, the medium comprising:
  (a) a nutrient medium with an energy source effective to support growth and reproduction of vancomycin-resistant *Enterococci*;
  (b) an effective amount of at least one agent selective to inhibit the growth of microorganisms other than vancomycin-resistant *Enterococci*;
  (c) a first chromogenic substrate incorporating a phosphate group and which is a substrate for a phosphatase enzyme produced by a first vancomycin-resistant *Enterococcus* species, said first chromogenic substrate producing a first detectable signal when in the presence of said first vancomycin-resistant *Enterococcus* species;
  (d) a second chromogenic substrate incorporating a galactopyranosyl moiety which is a substrate for a galactopyranoside enzyme produced by a second vancomycin-resistant *Enterococcus* species, said second chromogenic substrate producing a second detectable signal when in the presence of said second vancomycin-resistant *Enterococci* species and
  (e) a Krebs cycle intermediate that includes α-ketoglutaric acid and salts and derivatives thereof.

9. The medium of claim 8 wherein the Krebs cycle intermediate is further selected from at least one of the group comprising:
D-isocitric acid or salts thereof;
citric acid or salts thereof;
oxaloacetic acid or salts thereof;
malic acid or salts thereof;
fumaric acid or salts thereof;
succinic acid or salts thereof;
cis-aconitic acid or salts thereof; and succinyl-CoA.

10. The medium of claim 8 wherein the selective agent is selected from at least one of the group comprising: a glycopeptides antibiotic including teicoplanin; vancomycin; an antifungal compound; aztreonam; erythromycin; polymyxin B and salts thereof; cefoxitin; and amphotericin B.

11. The medium of claim 8 wherein the first chromogenic substrate is selected from the group consisting of 5-bromo-3-indolyl-phosphate disodium salt or p-toluidine salt; 5-bromo-4-chloro-3-indolyl-phosphate disodium salt or p-toluidine salt; 5-bromo-6-chloro-3-indolyl-phosphate disodium salt or p-toluidine salt; 6-chloro-3-indolyl-phosphate disodium salt or p-toluidine salt; 3-indolyl-phosphate disodium salt or p-toluidine salt; and fluorogens 6-fluoro-3-indolyl-phosphate disodium salt or p-toluidine salt; and 4-methylumbelliferyl-phosphate disodium salt or p-toluidine salt.

12. The medium of claim 11 wherein the first chromogenic substrate is 5-bromo-3-indolyl phosphate disodium salt.

13. The medium of claim 8 wherein the second chromogenic substrate is selected from the group consisting of 5-bromo-3-indolyl-a-galactopyranoside; 5-bromo-4-chloro-3-indolyl-a-galactopyranoside; 5-bromo-6-chloro-3-indolyl-a-galactopyranoside; 6-chloro-3-indolyl-a-galactopyranoside; 3-indolyl-a-galactopyranoside; fluorogens 6-fluoro-3-indolyl-a-galactopyranoside; and 4-methylumbelliferyl-a-galactopyranoside.

14. The medium of claim 13 wherein the second chromogenic substrate is 6-chloro-3-indolyl-α-galactopyranoside.

15. The medium of claim 8 further comprising an opacifying agent.

16. The medium of claim 15 wherein the opacifying agent is kaolin or titanium dioxide and the opacifying agent is present in a concentration range of between 0.1 g-5 g/L of medium.

17. The medium of claim 8 wherein the first *Enterococcus* species is *E. faecalis*.

18. The medium of claim 8 wherein the second *Enterococcus* species is *E. faecium*.

19. A method of screening for and differentiating between *E. faecalis* and *E. faecium* comprising inoculating a medium according to claim 8 with a biological specimen, incubating to obtain growth of *Enterococci* and examining the medium for the first and second detectable signals, wherein the first and second detectable signals differentiate between *E. faecalis* and *E. faecium*.

* * * * *